United States Patent [19]

Matsuzawa et al.

[11] Patent Number: 5,811,086

[45] Date of Patent: Sep. 22, 1998

[54] HAIR CARE PRODUCTS

[75] Inventors: Yukiyo Matsuzawa; Tatsuya Hattori, both of Kawasaki, Japan

[73] Assignee: Ajinomoto Co., Inc., Tokyo, Japan

[21] Appl. No.: 751,164

[22] Filed: Nov. 15, 1996

[30] Foreign Application Priority Data

Nov. 15, 1995 [JP] Japan .................................. 7-296432

[51] Int. Cl.⁶ .............................. A61K 7/06; A61K 7/11
[52] U.S. Cl. ................ 424/70.13; 424/70.1; 424/70.11; 424/70.21
[58] Field of Search .............................. 424/70.11, 70.13, 424/70.21, 70.1

[56] References Cited

U.S. PATENT DOCUMENTS

| | | | |
|---|---|---|---|
| 4,363,797 | 12/1982 | Jacquet et al. ............................ | 525/70 |
| 4,428,749 | 1/1984 | Morris ......................................... | 8/137 |
| 4,732,693 | 3/1988 | Hight ........................................ | 252/132 |
| 5,078,750 | 1/1992 | Komai ......................................... | 8/405 |
| 5,194,260 | 3/1993 | Grollier et al. ........................ | 424/401 |
| 5,328,690 | 7/1994 | Sikes ........................................ | 424/401 |

*Primary Examiner*—Sally Gardner-Lane
*Attorney, Agent, or Firm*—Oblon, Spivak, McClelland, Maier & Neustadt, P.C.

[57] ABSTRACT

A hair care product which exhibits an excellent setting power, an excellent use feeling, and improved solubility comprising the following ingredients (A), (B) and (C), (A) a polyacidic amino acid or its salt, (B) cationic cellulose, and (C) an ampholytic surfactant.

16 Claims, No Drawings

HAIR CARE PRODUCTS

BACKGROUND OF THE INVENTION

1. Field of the Invention

The present invention relates to a hair care product which comprises a polyacidic amino acid or its salt, cationic cellulose and an ampholytic surfactant, and which exhibits an excellent setting power, an excellent use feeling and improved solubility.

2. Description of the Background

Polyacidic amino acids such as polyaspartic acid, polyglutamic acid and the like exhibit a wettability (Japanese Laid-Open Patent Application (Kokai) No. 157,237/1994), and give a moist feeling and an excellent setting power to the hair when these compounds are mixed with hair care products such as a shampoo, a hair setting agent, a hair foam and the like. Meanwhile, cationic cellulose improve a rough feeling and give a smooth feeling to the hair. Accordingly, these are widely used in hair care products.

It was, however, found that when polyacidic amino acids are used in combination with cationic cellulose, insoluble complexes are formed and they cannot be dissolved. Such a problem did not occur when using a combination of polyacidic amino acids and cationic polymers other than cationic cellulose or a combination of anionic polymers other than polyacidic amino acids and cationic cellulose. It is an object of the present invention to provide a hair care product which exhibits an excellent setting power, an excellent use feeling and improved solubility.

SUMMARY OF THE INVENTION

In order to solve the above-mentioned problems, the present inventors have assiduously conducted investigations, and have consequently found that the combined use of a polyacidic amino acid, cationic cellulose and an ampholytic surfactant can give a hair care product in which an insoluble complex is not formed and solubility is therefore improved. This finding has led to the completion of the present invention.

That is, the present invention relates to a hair care product comprising (A) a polyacidic amino acid or its salt, (B) cationic cellulose, and (C) an ampholytic surfactant.

DETAILED DESCRIPTION OF THE INVENTION

The polyacidic amino acid which is used in the present invention includes polyaspartic acid and polyglutamic acid. The molecular weight thereof is not particularly limited, but it is preferably between approximately 500 to approximately 50,000 (degree of polymerization—between approximately 4 and approximately 430) with regard to the feeling property, especially preferably between approximately 1,000 and approximately 10,000 (degree of polymerization—between approximately 8 and approximately 90). Examples of the salt include salts of alkali metals such as sodium and potassium, amines such as diethanolamine and triethanolamine and amino acids such as arginine and lysine.

The cationic cellulose which is used in the present invention is not particularly limited. Cellulose which is obtained by reacting hydroxyethyl cellulose with 3-chloro-2-hydroxypropyltrimethylammonium chloride or glycidyltrimethylammonium chloride is preferable.

The ampholytic surfactant which is used in the present invention is not particularly limited. Examples thereof are as follows.

1) Betaine-type ampholytic surfactant:
   Carbobetaine-type surfactants such as alkyldimethylaminoacetate betaine and alkyl dihydroxyethylaminoacetate betaine; amidobetaine-type surfactants such as fatty acid amidopropyl dimethylaminoacetate betaine; hydroxysulfobetaine-type surfactants; amidosulfobetaine-type surfactants; and phosphobetaine-type surfactants.

2) Imidazoline-type ampholytic surfactant:
   2-Alkyl-N-carboxymethyl-N-hydroxyethylimidazolinium betaine, 2-alkyl-N-carboxyethyl-N-hydroxyethylimidazolinium betaine and 2-alkyl-N-sodiumcarboxymethyl-N-carboxymethyloxyethylimidazolinium betaine.

3) Alkylamino acid-type ampholytic surfactant:
   Laurylaminopropionic acid or its salt, laurylaminodipropionic acid or its salt, and β-alanine-type ampholytic surfactants such as N-alkyl-β-alanine.

The amounts of the ingredients in the hair care product of the present invention are mentioned below. The amount of the polyacidic amino acid or its salt (A) is between 0.05 and 15% by weight, preferably between 0.1 and 5% by weight; the amount of the cationic cellulose (B) is between 0.05 and 5% by weight, preferably between 0.1 and 3% by weight; and the amount of the ampholytic surfactant (C) is between 0.3 and 50% by weight, preferably between 0.9 and 10% by weight.

The formulation of the hair care product of the present invention is not particularly limited. The hair care product can be in the form of a liquid, a paste, a gel, a solid or a powder.

The hair care product of the present invention can contain, besides the above-mentioned essential ingredients, other additives which are usually incorporated in toiletries as required. Examples of other additives include anionic surfactants such as polyoxyethylenelauryl ether sodium sulfate; cationic surfactants such as stearyltrimethylammonium chloride and distearyltrimethylammonium chloride; nonionic surfactants such as glyceryl monostearate, sorbitan monopalmitate and polyoxyethylenecetyl ether; wetting agents such as propylene glycol, 1,3-butylene glycol, glycerin, sorbitol, pyroglutamic acid salts, amino acids and trimethylglycine; hydrocarbons such as liquid paraffins, petrolatum, solid paraffins, squalane and olefin oligomers; higher alcohols such as stearyl alcohol and cetyl alcohol; superfatting agents; antidandruff agents; disinfectants; anti-inflammatory agents; crude drugs; water-soluble polymers such as methyl cellulose, hydroxycellulose and partially deacetylated chitin; antiseptics such as paraben; UV absorbers; pearling agents; pH adjustors; perfumes; and pigments.

EXAMPLES

The present invention will be described more specifically by referring to the following Examples. However, the present invention is not limited thereto. In these Examples, the unit of the amount is % by weight.

Examples 1 to 3 and Comparative Examples 1 to 3

With respect to the following shampoos, the solubility was evaluated. The results are shown in Table 1.

(Evaluation Method)

The ingredients shown in Table 1 were heat-stirred at 70° C., and dissolved. The solution was allowed to stand at room temperature until the temperature of the solution reached a normal temperature. Then, the dissolved condition was visually observed, and evaluated according to the following standard.

○ : clearly dissolved x : precipitated or opaque

Examples 4 to 7 and Comparative Examples 4 to 6

A shampoo having the formulation shown in Table 2 was prepared in a usual manner, and an organoleptic test was conducted for this shampoo. The results are shown in Table 2.

(Evaluation Method)

Eight panelists washed the hair with the shampoo shown in Table 2. At this time, they evaluated the feeling organoleptically. The evaluation was conducted according to the following score.

good: 2 slightly good: 1 common: 0 slightly bad: −1 bad: −2

The average in this 5-grade evaluation was obtained. The results are as follows.

◎: 1.5 to 2.0

0: 0.5 to 1.4

Δ: −0.5 to 0.4 x : −2.0 to -0.6

TABLE 1

|  | Examples | | | Comparative Examples | | |
|---|---|---|---|---|---|---|
|  | 1 | 2 | 3 | 1 | 2 | 3 |
| polyoxyethylene-laurylether sodium sulfate | 15.0 | 15.0 | 15.0 | 15.0 | 15.0 | 15.0 |
| cocoyldiethanol-amide | 1.0 | 1.0 | 1.0 | 1.0 | 1.0 | 1.0 |
| cationic cellulose[1] | 1.0 | 1.0 | 1.0 | 1.0 | 1.0 | 1.0 |
| lauryl dimethyl-acetate betaine | 0.9 | | | | | |
| cocoyl amidopropyl-dimethylacetate betaine | | 1.2 | | | | |
| 2-alkyl-N-carboxymethyl-N-hydroxyimidazolinium betaine | | | 0.3 | | | |
| sodium polyaspartate (molecular weight 3600) | 1.0 | 1.0 | 1.0 | 1.0 | 1.0 | 1.0 |
| glycerin | 5.0 | 5.0 | 5.0 | 5.0 | 5.0 | 5.0 |
| antiseptic | 0.2 | 0.2 | 0.2 | 0.2 | 0.2 | 0.2 |
| purified water | * | * | * | * | * | * |
| Dissolved condition | ○ | ○ | ○ | X | X | X |

[1]"Leoguard GP" (a product of Lion Corporation)
*balance

TABLE 2

|  |  | Examples | | | | Comparative Examples | | |
|---|---|---|---|---|---|---|---|---|
|  |  | 4 | 5 | 6 | 7 | 4 | 5 | 6 |
| polyoxyethylene ether sodium sulfate | | 7.0 | 12.0 | | 7.0 | 12.0 | 7.0 | 15.0 |
| coconut oil fatty acid glycine potassium | | 5.0 | | 5.0 | 5.0 | | 5.0 | |
| lauric acid diethanolamide | | 1.5 | 1.5 | 1.5 | 1.5 | 1.5 | 1.5 | 1.5 |
| lauryl dihydroxyethylacetate betaine | | 5.0 | | | | 5.0 | | |
| lauric acid amidopropyldimethyl acetate betaine | | | 3.0 | | 2.0 | | 3.0 | |
| 2-alkyl-N-carboxyethyl-N-hydroxyethylimidazolinium betaine | | | | 8.0 | | | | |
| cationic cellulose[1] | | 1.5 | 1.5 | 1.5 | 1.5 | 1.5 | | |
| sodium polyaspartate (molecular weight 4200) | | 3.0 | 2.0 | 3.0 | 1.0 | | 2.0 | 3.0 |
| trimethylglycine | | 1.5 | 1.5 | 1.5 | 1.5 | 1.5 | 1.5 | 1.5 |
| 1,3-butylene glycol | | 5.0 | 5.0 | 5.0 | 5.0 | 5.0 | 5.0 | 5.0 |
| antiseptic | | 0.2 | 0.2 | 0.2 | 0.2 | 0.2 | 0.2 | 0.2 |
| purified water | | * | * | * | * | * | * | * |
| Organoleptic evaluation | Rough feeling in rinsing | ◎ | ◎ | ○ | ◎ | ○ | Δ | Δ |
| | Finger-combing in rinsing | ◎ | ◎ | ○ | ○ | Δ | ○ | x |
| | Moist feeling after drying | ◎ | ◎ | ◎ | ◎ | Δ | Δ | ○ |
| | Dry feeling after drying | ◎ | ◎ | ◎ | ○ | ○ | ○ | Δ |

[1]"Polymer JR400" (a product of Amerchol Corporation)
*balance

Example 8

The ingredients shown in Table 3 were heat-stirred, and dissolved. Then, the mixture was stirred at room temperature until the temperature of the mixture reached a normal temperature. The resulting shampoo exhibited excellent solubility. It was also excellent in terms of a rough feeling in rinsing, a moist feeling after drying and a dry feeling after drying.

TABLE 3

Hair shampoo

| | |
|---|---:|
| sodium cocoylglutamate | 8.0 |
| lauroyl-N-methyl-β-alanine sodium | 4.0 |
| 2-alkyl-N-carboxymethyl-N-hydroxyethylimidazolinium betaine | 2.0 |
| cationic cellulose[1] | 1.2 |
| pqlyoxyethylene (40) hardened castor oil | 1.0 |
| sodium pyroglutamate | 0.5 |
| 1,3-butylene glycol | 5.0 |
| potassium polyaspartate (molecular weight 4200) | 3.0 |
| citric acid | suitable amount |
| antiseptic | suitable amount |
| purified water | balance |
| Total | 100.0 |

[1]"Polymer JR400"

Example 9

The ingredients shown in Table 4 were heat-stirred at 70° C, and dissolved. Then, the mixture was gradually cooled to 30° C. while being stirred to obtain a product. The resulting hair lotion exhibited an excellent solubility. It as also excellent in terms of a moist feeling after drying and a dry feeling after drying.

TABLE 4

Hair lotion

| | |
|---|---:|
| pyroglutamic acid isostearic acid polyoxyethyleneglyceryl | 0.5 |
| lauroyl glutamate-di (cholesteryloctyldodecyl) mixed ester | 0.5 |
| cationic cellulose[1] | 1.0 |
| sodium laurylaminodipropionate solution (30%) | 3.0 |
| 1,3-butylene glycol | 3.0 |
| sodium polyaspartate (molecular weight 3600) | 1.2 |
| N-lauroyl lysine | 0.2 |
| wetting agent [2] | 0.5 |
| antiseptic | suitable amount |
| distilled water | balance |
| Total | 100.0 |

[1]"Leoguard GP"
[2] "Prodew 400" (a product of Ajinomoto Co., Inc.)

Example 10

The ingredient (a) shown in Table 5 was gradually added to the ingredients (b) shown in Table 5 which had been heat-dissolved at 80°, and the mixture was emulsified using a homogenizer. The emulsion was added to the ingredients (c) shown in Table 5, and the mixture was gradually cooled to 30° C. while being stirred to obtain a stock solution. This stock solution was filled in a spray can, and a valve was mounted on the spray can. A gas was then charged therein. The resulting hair foam exhibited excellent solubility, and was also excellent in terms of a moist feeling after drying and a dry feeling after drying.

TABLE 5

Hair foam (Formulation of a stock solution)

| | |
|---|---:|
| (a) ingredient | |
| dimethylsiloxane | 5.0 |
| (b) ingredients | |
| dipropylene glycol | 7.0 |
| polyoxyethylene hardened castor oil | 1.0 |
| (c) ingredients | |
| hydroxysulfobetaine-type surfactant | 5.0 |
| cationic cellulose[1] | 2.5 |
| sodium polyaspartate (molecular weight 3600) | 2.0 |
| hydrolyzed collagen | 0.5 |
| ethanol | 15.0 |
| antiseptic | suitable amount |
| purified water | 62.0 |
| Total | 100.0 |

(Formulation of filling)

| | |
|---|---:|
| stock solution | 90.0 |
| liquefied petroleum gas | 10.0 |

[1]"Leoguard GP"

The disclosure of Japan priority patent application No. 296432/1995, filed Nov. 15, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A composition comprising the following ingredients (A), (B) and (C),
    (A) 0.1–5% of a polyacidic amino acid selected from the group consisting of polyaspartic acid and polyglutamic acid, or its salt,
    (B) 0.1–3% of cationic cellulose obtained by reacting hydroxyethyl cellulose with 3-chloro-2-hydroxypropyltrimethylammonium chloride or glycidyltrimethylammonium chloride, and
    (C) 0.9–10% of an ampholytic surfactant.

2. The composition of claim 1, wherein the molecular weight of (A) is 500–50,000.

3. The composition of claim 2, wherein the molecular weight of (A) is 1,000–10,000.

4. The composition of claim 1, wherein the polyacidic amino acid is polyaspartic acid.

5. The composition of claim 1, wherein the polyacidic amino acid is polyglutamic acid.

6. The composition of claim 1, wherein the cationic cellulose is obtained by reacting hydroxyethyl cellulose with 3-chloro-2-hydroxypropyltrimethylammonium chloride.

7. The composition of claim 1, wherein the cationic cellulose is obtained by reacting hydroxyethyl cellulose with glycidyltrimethylammonium chloride.

8. The composition of claim 1, wherein the ampholytic surfactant is a betaine ampholytic surfactant, an imidazoline ampholytic surfactant, or an alkylamino acid ampholytic surfactant.

9. The composition of claim 8, wherein the ampholytic surfactant is a betaine ampholytic surfactant selected from the group consisting of a carbobetaine surfactant; an amidobetaine surfactant; a hydroxysulfobetaine surfactant; an amidosulfobetaine surfactant; and a phosphobetaine surfactant.

10. The composition of claim 9, wherein the betaine ampholytic surfactant is a carbobetaine surfactant selected from the group consisting of alkyldimethylaminoacetate betaine and alkyl dihydroxyethylaminoacetate betaine.

11. The composition of claim 9, wherein the betaine ampholytic surfactant is an amidobetaine surfactant.

12. The composition of claim 11, wherein the amidobetaine surfactant is fatty acid amidopropyl dimethylaminoacetate betaine.

13. The composition of claim 8, wherein the ampholytic surfactant is an imidazoline ampholytic surfactant.

14. The composition of claim 13, wherein the imidazoline ampholytic surfactant is selected from the group consisting of 2-Alkyl-N-carboxymethyl-N-hydroxyethylimidazolinium betaine, 2-alkyl-N-carboxyethyl-N-hydroxyethylimidazolinium betaine and 2-alkyl-N-sodiumcarboxymethyl-N-carboxymethyloxyethylimidazolinium betaine.

15. The composition of claim 8, wherein the ampholytic surfactant is an alkylamino acid ampholytic surfactant.

16. The composition of claim 15, wherein the alkylamino acid ampholytic surfactant is selected from the group consisting of laurylaminopropionic acid or its salt, laurylaminodipropionic acid or its salt, and N-alkyl-β-alanine.

* * * * *